US009474662B2

(12) United States Patent
Andersson et al.

(10) Patent No.: US 9,474,662 B2
(45) Date of Patent: Oct. 25, 2016

(54) DISPOSABLE ARTICLE COMPRISING NON HOOK COMPATIBLE AREAS

(71) Applicant: SCA Hygiene Products AB, Gothenburg (SE)

(72) Inventors: Mikael Andersson, Gothenburg (SE); Sofia Hermansson, Vastra Frolunda (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 0 days.

(21) Appl. No.: 14/427,661

(22) PCT Filed: Oct. 4, 2012

(86) PCT No.: PCT/SE2012/051061
§ 371 (c)(1),
(2) Date: Mar. 12, 2015

(87) PCT Pub. No.: WO2014/054989
PCT Pub. Date: Apr. 10, 2014

(65) Prior Publication Data
US 2015/0245960 A1    Sep. 3, 2015

(51) Int. Cl.
*A61F 13/15* (2006.01)
*A61F 13/62* (2006.01)
*A61F 13/56* (2006.01)

(52) U.S. Cl.
CPC ......... *A61F 13/625* (2013.01); *A61F 13/5638* (2013.01); *A61F 13/622* (2013.01);
(Continued)

(58) Field of Classification Search
CPC .... A61F 13/62; A61F 13/622; A61F 13/627; A61F 13/565; A61F 13/56; A61F 13/5655; A61F 2013/5677

USPC ........ 604/387, 389, 391, 390, 392, 394, 396
See application file for complete search history.

(56) References Cited

U.S. PATENT DOCUMENTS

| 5,266,453 A | 11/1993 | Matushita et al. |
| 5,971,970 A | 10/1999 | Carlbark et al. |

(Continued)

FOREIGN PATENT DOCUMENTS

| EP | 0 528 282 A2 | 2/1993 |
| WO | WO 94/26224 A1 | 11/1994 |

(Continued)

OTHER PUBLICATIONS

International Search Report (PCT/ISA/210) mailed on Jun. 19, 2013, by the Swedish Patent Office as the International Searching Authority for International Application No. PCT/SE2012/051061.

(Continued)

*Primary Examiner* — Jacqueline Stephens
(74) *Attorney, Agent, or Firm* — Buchanan Ingersoll & Rooney PC (57) ABSTRACT

The invention relates to a disposable article having a longitudinal direction, a longitudinal center line and a transverse direction, wherein the article has a first and a second longitudinal edge, a first and a second transverse edge, wherein the article comprises a first covering layer comprising a first surface intended to face towards the user and a second surface intended to face away from the user in use, wherein at least a first and a second fixing member comprising hook elements are arranged on the first surface close to the first transverse edge, wherein the first fixing member is arranged close to the first longitudinal edge and the second fixing member is arranged close to the second longitudinal edge, wherein substantial parts of the first surface are compatible with the hook elements.

12 Claims, 4 Drawing Sheets

(52) U.S. Cl.
CPC ............. *A61F 13/56* (2013.01); *A61F 13/565* (2013.01); *A61F 13/5655* (2013.01); *A61F 13/62* (2013.01); *A61F 13/627* (2013.01); *A61F 2013/5677* (2013.01)

(56) References Cited

U.S. PATENT DOCUMENTS

| | | |
|---|---|---|
| 2002/0032428 A1 | 3/2002 | Lindstrom et al. |
| 2005/0143709 A1 | 6/2005 | Lindstrom |
| 2010/0256588 A1 | 10/2010 | Vigmo |

FOREIGN PATENT DOCUMENTS

| | | |
|---|---|---|
| WO | WO 99/21522 A1 | 5/1999 |
| WO | 2006/123976 A1 | 11/2006 |
| WO | 2009/048360 A1 | 4/2009 |
| WO | WO 2012/050740 A1 | 4/2012 |

OTHER PUBLICATIONS

Written Opinion (PCT/ISA/237) mailed on Jun. 19, 2013, by the Swedish Patent Office as the International Searching Authority for International Application No. PCT/SE2012/051061.

International Preliminary Report on Patentability (PCT/IPEA/409) mailed on Feb. 17, 2015 for International Application No. PCT/SE2012/051061.

European Search Report issued May 3, 2016, by the European Patent Office, in corresponding European Patent Application No. 12886116.8 (5 pages).

DISPOSABLE ARTICLE COMPRISING NON HOOK COMPATIBLE AREAS

TECHNICAL FIELD

The invention relates to a disposable article having a longitudinal direction, a longitudinal centre line and a transverse direction, wherein the article has a first and a second longitudinal edge, a first and a second transverse edge, wherein the article comprises a first covering layer comprising a first surface intended to face towards the user and a second surface intended to face away from the user when in use, wherein at least a first and a second fixing member comprising hook elements are arranged on the first surface close to the first transverse edge, wherein the first fixing member is arranged close to the first longitudinal edge and the second fixing member is arranged close to the second longitudinal edge, wherein substantial parts of the first surface are compatible with the hook elements. The invention relates to a type of disposable article having a belt permanently joined to one end area of the disposable article, wherein the two corners of the opposing end area have fixing members comprising hook elements on the surface that is intended to face towards the user.

Such an article is put on a user by first applying the belt around the waist and then detachably fastening the hook elements of the opposing end area to the outwardly oriented surface of the belt. The outside of the belt has loops in this case with which the hook elements are compatible, i.e. the hook elements can attach to the belt.

The invention also relates to a type of disposable article having at least one fixing member comprising hook elements in each corner on the surface intended to face towards the user. The hook elements of the fixing members are thereby intended to detachably anchor the respective corner to a separate belt arranged around a user's waist.

BACKGROUND

Disposable articles of the type described above are well known, both in the form of disposable articles as a replacement for traditional underwear and in the form of absorbent articles intended for incontinent persons.

A special type of article is intended to be fastened detachably to a separate belt arranged around a user's waist.

The international PCT application WO 1994/26224 and the later application with application number 2012/050740 describe such absorbent disposable articles comprising hook elements at each corner on the surface intended to face towards the user. The documents describes how the 4 hook elements, placed at each corner of the article, are fastened detachably to a separate belt that surrounds the user's waist when the article is put on said user.

Another type of commonly occurring disposable articles consists of so-called belt articles. A belt article is characterised in that it comprises a transverse belt permanently joined to the article, either at the article's front or rear transverse edge. The surface that is intended to face towards the user when the article is in use has in this case, at the opposing transverse edge, hook elements intended to be connected detachably to the belt. At least one hook element is arranged here in the respectively opposing corner. On application of such a belt article, the belt is fixed, in a first stage, around the user's waist. The opposing free transverse edge is then led in between the user's legs and fastened to the outside of the belt. The hook elements are intended to be fastened to the side of the belt that is oriented away from the user. Special receiving surfaces on the belt designed to cooperate with the hook elements are common. It is also common that the entire belt is manufactured from a material that can cooperate with the hook elements, wherein no special receiving surfaces are arranged on the belt.

Absorbent belt articles, so-called belt diapers, are described in several different patent documents. For example, belt diapers are described in the international patent applications WO 1999/21522 and WO 1994/26224.

Regardless of whether the article is intended to be fastened to a separate belt or it is a so-called belt article, the same problem arises on application. The problem consists in that the corners of the article have a tendency to fold in over the surface of the covering layer that is intended to face towards the user when in use and attach to the fibre loops on the covering layer. Several different types of covering layer intended to rest against the user's abdomen consist of fibrous nonwoven layers comprising fibre loops, on which the hook elements easily get caught in an undesirable manner. The result is that difficulties arise in finding and releasing the article's corners/hook elements when the article is put on a user.

There is thus a need for an improved disposable article, both of the type that is intended to be used together with a separate belt and of the type that comprises a permanent belt at one transverse edge, where the hook elements that are intended to be connected to the belt are easily accessible/ easy to find.

SUMMARY OF THE INVENTION

A disposable article of the type mentioned in the introduction has been achieved with the present invention, however, wherein the product substantially avoids the problems stated at the beginning that were associated with previous such articles.

A disposable article produced according to the invention is distinguished primarily in that the first surface of the covering layer comprises a first area connected to a first fixing member and a second area connected to a second fixing member, wherein said areas have substantially lower compatibility with the respective hook elements than adjoining parts of the covering layer's first surface.

Because the compatibility between the hook elements of the fixing member and the covering layer is substantially lower in said adjacent areas, the risk of the hook elements catching on these areas is considerably reduced. If, contrary to expectation, the hook elements should attach against the first surface of the covering layer that is oriented towards the body, the release force is at least greatly reduced.

According to one aspect of the invention, the areas that have substantially lower compatibility with the respective hook elements are characterised by an extension in the longitudinal direction of the article, substantially from the first transverse edge towards the opposing transverse edge, of 10-20%, preferably 15% of the article's outstretched length. In the transverse direction of the article, the first area has an extension between the article's first longitudinal edge and the longitudinal centre line of 25-50%, preferably 37% of the outstretched length of the first transverse edge, and the second area has an extension in a transverse direction between the second longitudinal edge and the longitudinal centre line of 25-50%, preferably 37% of the outstretched length of the first transverse edge. It has turned out that, in the overwhelming number of cases when the corners of a disposable article are folded over the covering layer intended to face towards the user, the respective hook elements end up inside the adjacent area defined above.

According to one aspect of the invention, the areas entirely lack compatibility with the hook elements. The hook elements cannot, therefore, according to this aspect of the invention, firmly attach against the areas that entirely lack compatibility with the hook elements.

Another aspect of the invention is characterised in that the disposable article comprises a substantially liquid-impermeable second covering layer that is arranged on the second surface of the first covering layer oriented away from the user. A substantially liquid-impermeable second covering layer protects articles of clothing lying outside from being contaminated if the user should happen to excrete minor quantities of urine, faeces or discharges. For example, an article comprising a substantially liquid-impermeable second covering layer is particularly valuable in the days before menstruation as extra security.

According to one aspect, the invention is characterised in that an absorbent body is arranged between the first covering layer and the substantially liquid-impermeable second covering layer, wherein the first covering layer is substantially liquid-permeable.

With an absorbent body arranged between the covering layers, the disposable article is suitable for use for larger secretions of urine, faeces or menstruation fluid by the user, for example. For such a disposable article to function, the urine or menstruation fluid must naturally be able to enter the absorption body, which is why the first covering layer oriented towards the user is liquid-permeable.

An aspect of the invention is characterised in that the article is intended to be attached detachably to a separate belt arranged around a user's waist. The article comprises in this case a third and a fourth fixing member comprising hook elements arranged on the first surface adjacent to the second transverse edge, wherein the third fixing member is arranged adjacent to the second longitudinal edge and the fourth fixing member is arranged adjacent to the first longitudinal edge. According to this aspect of the invention, the first surface of the first covering layer comprises a third area connected to the third fixing member and a fourth area connected to the fourth fixing member, wherein said areas have a substantially lower compatibility with the respective hook elements than adjacent parts of the first surface of the covering layer. The advantages of an article that is fixed to a separate belt are many, for example material is saved, since the belt can be used for several exchanges of the remaining part. Another advantage is that it is often simpler to change the article on certain bedridden users, since it is not necessary to encircle the bedridden user's waist when making the change.

An aspect of the invention is characterised in that the third and fourth area that have substantially lower compatibility with the respective hook elements have an extension in the article's longitudinal direction substantially from the second transverse edge towards the opposing transverse edge of 10-20%, preferably 15% of the article's outstretched length. The third area further has an extension in the transverse direction of the article between the second longitudinal edge and the longitudinal centre line of the article of 25-50%, preferably 37% of the outstretched length of the second transverse edge, the fourth area having an extension in the transverse direction of the article between the first longitudinal edge and the article's centre line of 25-50%, preferably 37% of the outstretched length of the second transverse edge.

According to an aspect of the invention, the third and fourth area entirely lack compatibility with the respective hook elements.

An aspect of the invention relates to a disposable article comprising a belt arranged connected to the second transverse edge of the article, wherein the belt is intended to be fastened around the user's waist when in use, wherein the hook elements are intended to be connected, when in use, detachably to the surface of the belt oriented away from the user.

Another aspect of the invention is characterised in that the first covering layer consists of a nonwoven material comprising heat-treatable synthetic fibres that have loops on the first surface. The loops in the respective area that has substantially lower compatibility with the respective hook elements have been substantially reduced by heat treatment. For covering layers that consist of nonwoven material comprising fusible fibres, it is a relatively simple process to reduce or even eliminate the loops by heat-sealing the areas where it is not desired for any hook elements to attach.

According to an aspect of the invention, the first covering layer consists of a nonwoven material that has loops on the first surface. The loops in the respective area that has substantially lower compatibility with the respective hook elements have been eliminated by laminating a cover layer substantially free of loops on the first surface in the respective area, wherein the cover layer can consist, for example, of a spunbond nonwoven or of a plastic film.

DESCRIPTION OF EMBODIMENTS

The invention relates on the one hand to a disposable article of the belt type, a so-called belt article, the article comprising a transverse belt and a chassis part. Belt articles are characterised in that they comprise a transverse belt connected to either the front or rear end part of the article's chassis part. When applying such a belt article, the belt is fixed in a first stage around the user's waist. The chassis part of the belt article is hanging loosely from the belt in this case. The chassis part is then led between the user's legs and attached to the belt, wherein the belt comprises fixing surfaces intended to stick fast to the fixing member arranged on the chassis part by its free transverse edge.

The invention also relates to a disposable article intended to be fixed to a separate belt that is applied around the waist of a user. The disposable article has fixing members at all its corners that are intended to be connected detachably to fixing surfaces arranged on the surface of the belt oriented away from the user.

Figure 1:
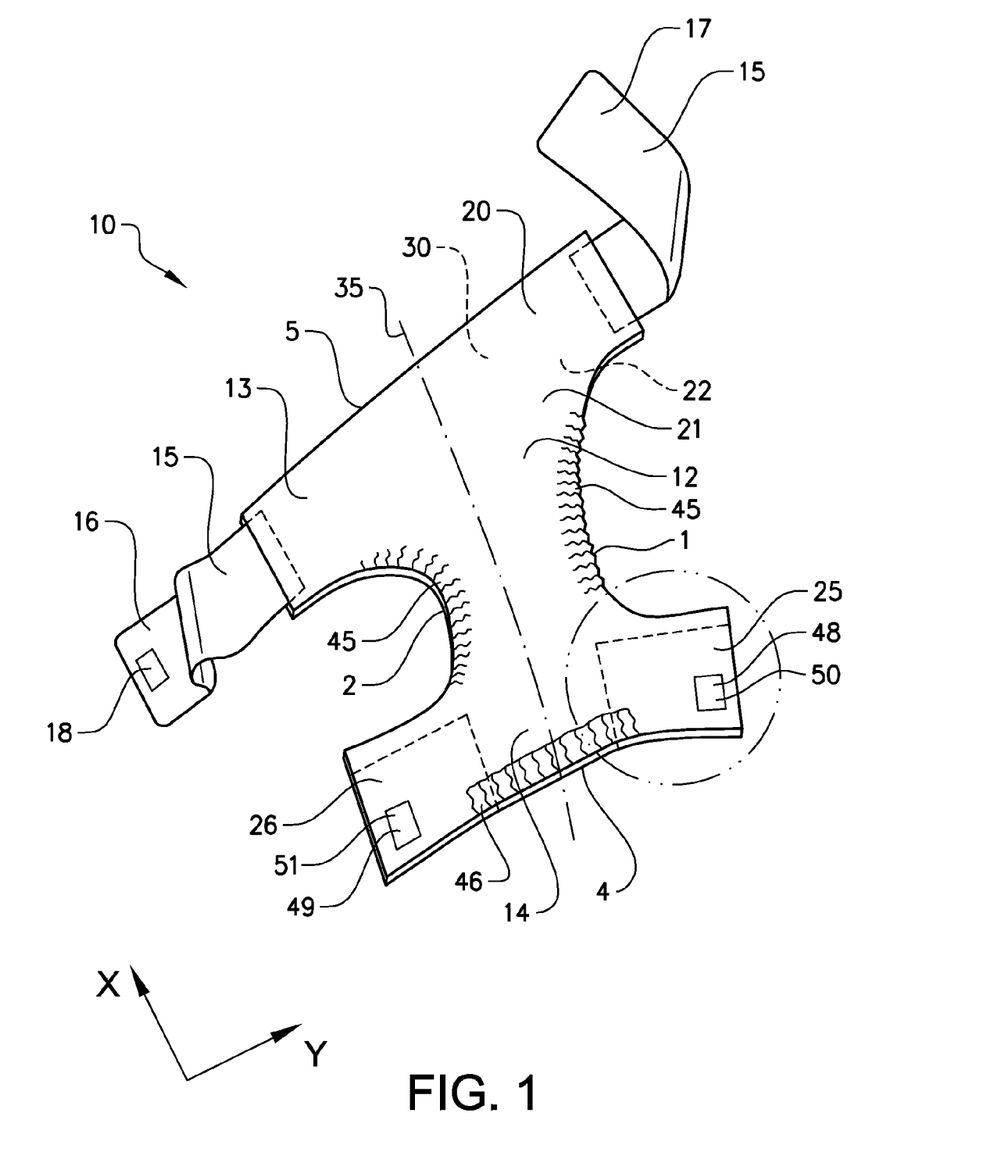
FIG. 1 shows a so-called belt article according to the invention from the side that is intended to face towards the user when in use.

FIG. 1 shows substantial components of a belt article 10 according to the invention, wherein the belt article 10 is shown from the side which is intended to face towards the user when in use.

The belt article 10 has a longitudinal direction X and a transverse direction Y and comprises an elastic belt 15 and a chassis part 12 comprising a first covering layer 20. The elastic belt 15 of the belt article 10 is intended to encircle a user's waist, wherein the belt 15 has a first belt half 16 and a second belt half 17. The belt halves 16, 17 extend in the transverse direction Y of the belt diaper. The belt halves 16, 17 are connected to the chassis part 12 in the rear end part 13, wherein the first belt half 16 is joined to the longitudinal edge 2 and the second belt half 17 is joined to the opposing longitudinal edge 1. The first belt half 16 comprises a fixing member 18 for fixing the belt around a user's waist, wherein the fixing member comprises a Velcro surface that cooperates with the second belt half 17 when in use.

Alternatively, it is conceivable that the fixing member 18 arranged on the first belt half 16 consists of an adhesive surface, wherein the second belt half 17 comprises a suitable receiving surface for the adhesive surface.

The name belt half does not mean that the two belt halves must be of the same length. In alternative embodiments, one belt half can be longer than the other. It is important, however, that the combined length of the two belt parts reaches around a user's waist.

In an alternative aspect of the invention, the two belt halves 16, 17 of the belt article 10 can consist of only one piece of material, which piece of material extends in the transverse direction Y across the entire rear end part 13 and past the respective longitudinal edges 1, 2.

In another alternative aspect of the invention, it is conceivable that the belt article 10 has only one belt part, wherein the belt part extends in the transverse direction past only one of the longitudinal edges 1, 2 of the belt article 10. In such an aspect of the invention the one belt part has a length that permits the belt part to reach around the waist of a user.

The belt 15 can, in accordance with other alternative aspects of the invention, be inelastic or partly elastic. Partly elastic belt 15 means that certain parts of the length of the belt 15 have elastic properties, while certain other parts of the length of the belt do not have elastic properties.

The belt article 10 comprises a first covering layer 20, wherein the covering layer comprises a first surface 21, intended to face towards the user when the belt article 10 is used, and an opposing second surface 22. The first covering layer 20 of the belt article 10 preferably has an hourglass shape, but other shapes such as a rectangular shape, for example, also occur.

The first covering layer 20 can consist of any material suitable for the purpose. The most common breathable covering materials for disposable articles are nonwoven textile materials, so-called nonwoven materials manufactured according to various methods. Not so common but also occurring is the use of covering layers 20 of woven material or net material. For example, a nonwoven material suitable as a covering layer 20 can be manufactured from synthetic fibres such as polyester or polypropylene, of natural fibres such as cotton fibres. A mix of synthetic and natural fibres also occurs. The manufacture of a nonwoven material consists of the two main stages web formation and web bonding. Web formation means that a web is created of as even a surface weight as possible, wherein the web can be created by carding of natural or manmade staple fibres. The spunlaid technique is another web-forming technique, in which polymer material is extruded to thin continuous fibre threads on a continuous conveyor. The extruded thin fibre threads are randomised following extrusion in that they land on the continuous conveyor in a random manner. Web formation can take place in several different ways. A commonly occurring method is so-called thermal bonding, wherein a bonding pattern is melted into the fibre web in a roller nip where at least one of the hot rollers has a pattern. For web formation by means of thermal bonding to work, at least a certain portion of the fibres in the web must consist of synthetic fusible fibres. Occurring bonding patterns are dots of varying geometry, small rectangular or circular surfaces, floral patterns or the like.

Another web bonding method, so-called print bonding, means the web is bonded pointwise, for example, using adhesive material. Alternative patterns instead of pointwise bonding also exist for this method. Another method that is used is pinning of the fibre web. The fibre web is bonded together in this method by guiding pins provided with flukes forward and back through the fibre web, so that the fibres in the web are entangled, wherein the bonding is obtained.

According to one variant, so-called hydroentangling, the fibre web is entangled and bonded by spraying fine water jets under high pressure through the web from both directions.

What is common to the methods described above, and also to other methods, is that not all the surface of the covering layer 20 is bonded, but between the bonding areas the covering layer has open areas comprising fibre threads that are fixed at one or both of their ends to the adjacent bonded areas. The areas comprising such free fibre threads fixed at both their ends act as good receiving areas for hook elements in a Velcro connection, a so-called hook& loop connection, wherein said areas constitute loop elements.

Covering layers 20 that consist of continuous thin fibres that extend mainly in a longitudinal or transverse direction of the product also exist. This type of covering layer 20 also comprises areas that act as good receiving areas for hook elements in a Velcro connection.

Laminate consisting of two or more of the aforementioned possible covering materials also occur, such as a covering consisting of different materials in different parts of the surface. It also occurs that the covering layer 20 consists of an entirely or partially elastic material to give the belt article 10 a better fit when in use. The covering layer 20 also has a first and a second fixing member 48, 49 arranged at the respective longitudinal edge 1, 2 in the front end part 14 of the covering layer 20, i.e. connected to the two front corners of the covering layer 20. The fixing members 48, 49 are arranged on the side of the covering layer 20 that is intended to face towards the user when the belt article 10 is used.

The fixing members 48, 49 comprise hook elements 50, 51 that are intended, on application of the belt article 10 to a user, to be connected detachably to loops arranged on the side of the belt 15 that is intended to face away from the user. In alternative aspects of the invention, the fixing members 48, 49 can consist of separate fastening tabs that are connected permanently to the front end part 14 of the belt article 10, wherein the fastening tabs extend outside the edges of the belt article 10. The hook elements 50, 51 are arranged in this case on the fastening tabs.

When a belt article 10 is to be applied to a user, the belt 15 is first fixed around the user's waist. The front end part 14 of the belt article 10 that hangs loosely is then led in between the user's legs, following which the fixing members

48, 49 are fixed to the belt 15 on the stomach on the side of the belt 15 oriented away from the user. The hook elements 50, 51 are fixed in this case to loops arranged on the surface of the belt 15 oriented away from the user. A belt article is also conceivable in which the belt is connected to the front end part of the belt article. Such an article is applied to the user in the reverse manner, i.e. after the belt has been fixed around the user's waist, the loosely hanging rear end part is led in between the user's legs and fixed to the belt at the back on the side of the belt oriented away from the user.

To improve the fit of the belt article 10, the longitudinal edges 1, 2 of the first covering layer 20 can be provided with leg elastic 45 arranged substantially in the longitudinal direction X of the article. The task of the leg elastics 45 includes improving the fit of the article, and making the belt article 10 more like textile multiple-use briefs/pants. The respective leg elastic 45 can consist of one or more elastic threads that in the extended state have been joined to the covering layer 20 by gluing, ultrasonic welding or the like. Alternatively, the respective leg elastic 45 can consist of elastic ribbon material of foamed material, for example. The respective leg elastic 45 is preferably arranged on the side of the first covering layer 20 that is intended to face away from the user when in use.

The rear or front end part 13, 14 of the belt article 10 can also be provided with so-called waist elastic 46 in the form of elastic elements arranged along the second transverse edge 5 or first transverse edge 4 of the belt article 10 to give the belt article 10 a soft, flexible enclosure of the user's waist. In FIG. 1, only the front end part 14 of the belt article 10 is provided with waist elastic 46.

The waist elastic 46 consists of a thin strip of elastic foam material that is attached by glue to the side of the first covering layer 20 that is intended to face away from the user. The waist elastic 46 is applied in a stretched state to achieve a holding-together force that stretches the belt article 10 around the user's waist. When the fixing members 48, 49 are fastened to the belt 15, it is suitable that the waist elastic 46 is tensioned in the transverse direction Y of the belt article 10 so that the front end part 14 has a smooth configuration over the user's stomach on use.

According to another aspect of the invention, the belt article 10 comprises a second covering layer 30 arranged on the side of the first covering layer 20 that is intended to face away from the user when in use. The second covering layer 30 has the same extension in the X/Y plane as the first covering layer 20. The second covering layer 30 is preferably substantially liquid-impermeable, but other types of covering layer can also exist.

The second covering layer 30 can consist of a range of different materials, but most frequently it consists of a thin, preferably liquid-impermeable plastic film, but it is also possible to use other types of substantially liquid-impermeable material such as nonwoven material, for example, that has been made substantially liquid-impermeable through plastic coating, for example, a liquid-impermeable foam layer, liquid-impermeable glue or the like. The second covering layer 30 can alternatively consist of a liquid-impermeable vapour-permeable material, a so-called breathable material.

Furthermore, laminates comprising at least one liquid-impermeable and preferably breathable layer arranged against the second surface 22 of the first covering layer 20 also exist as a second covering layer 30. These laminates usually consist of a liquid-impermeable material acting as a barrier against soaking through and a more textile-like material arranged on the side of the belt article 10 that is oriented away from the user on use. The outside of the belt article 10 is thereby more garment-like on use. The textile-like layer of the laminate normally consists of a nonwoven layer, but other textile or textile-like materials also exist. The first covering layer 20 and the second liquid-impermeable covering layer 30 can be joined to one another in several different ways. Examples of joining methods are gluing, thermal fusing, ultrasonic welding or the like. For belt articles 10 comprising a first covering layer 20 and a substantially liquid-impermeable second covering layer 30, it is suitable for the leg elastic 45 and the waist elastic 46 described above to be arranged between the two covering layers 20, 30. The first covering layer 20 can, in a belt article 10 comprising a liquid-impermeable second covering layer 30, have a low absorption capacity wherein smaller bodily secretions such as occasional drops of urine, for example, initially secreted menstruation fluid or similar.

According to an aspect of the invention, the belt article 10 has an absorption body 40 arranged between the first covering layer 20 and the second substantially liquid-impermeable covering layer 30. The first covering layer 20 of a belt article according to this aspect must be liquid-permeable. The belt article 10 in accordance with this aspect of the invention relates to a diaper intended to be used by an incontinent adult person or by a child who has not yet become continent. The absorption body 40 has substantially the same profile, but a smaller surface, than the first and second covering layers 20, 30. The two covering layers 20, 30 thus extend outside the edges of the absorption body 40 along the entire circumference of the absorption body 40. The absorption body 40 has, exactly like the covering layers 20, 30, a front and a rear end part and a narrower crotch part located between the end parts. Upon use of a belt article 10 comprising an absorption body 40, the front part of the crotch part and the front end part principally act like a receiving area for urine, while the rear part of the crotch part and the rear end part act mainly as a receiving area for faeces. The liquid-permeable first covering layer 20 and the substantially liquid-impermeable second covering layer 30 are connected to one another outside the absorption body 40 along its entire circumference.

The absorption body 40 can be constructed from one or more layers of cellulose fluff pulp. The cellulose fluff pulp can be mixed with fibres or particles of a highly absorbent polymer material, so-called super absorbents, of the type that chemically binds large quantities of fluid on absorption with the formation of a fluid-holding gel. The absorption body 40 can also comprise highly absorbent polymer material arranged in a layer inside the absorption body or connected to the surface or surfaces of the absorption body. The absorption body 40 can further include further components for improving the properties of the absorption body 40. Examples of such components are binding fibres, various types of fluid-dispersing layers or fibres, dimensionally stabilising components, reinforcing fibres or the like. The absorption body 40 can naturally also consist of other types of absorption material, such as absorbent nonwoven material, absorbent foam, textile materials, peat or blends of different kinds of absorption material. Special layers for quickly taking up large quantities of liquid and temporarily holding this liquid in order then to discharge the temporarily stored liquid to other parts of the absorption body 40 can also be included in belt articles 10 according to this aspect of the invention. Such receiving layers are normally arranged between the first liquid-permeable covering layer 20 and the absorption body 40. No receiving layer is shown in FIG. 1.

The belt article 10 is distinguished primarily in that the first surface 21 of the first covering layer 20 comprises a first area 25 connected to the first fixing member 48 and a second area 26 connected to the second fixing member 49, wherein said areas 25, 26 have substantially lower compatibility with the respective hook elements 50, 51 than adjacent parts of the first surface 21 of the covering layer 20. A belt article 10 is exposed to a large number of handling stages from leaving the production machine right up to it being placed on a user. When the belt article 10 is packed, it is handled/folded first in one or more stages, following which it is then automatically inserted into the packaging with which the end customer/user later comes into contact. When the end customer/user removes a belt article 10 from an open pack and applies it to a user (or to themselves), the belt article 10 is exposed to a number of manual handling stages.

The handling stages are thus both automatic during packaging and manual when applying the belt article 10 to a user. The relatively flexible front corners of the belt article 10 comprising the fixing members 48, 49 have, in the various handling stages, a tendency to fold over the first surface 21 of the first covering layer 20 of the belt article 10, wherein the hook elements 50, 51 come into contact with the first surface 21 of the first covering layer 20.

Figure 2A:
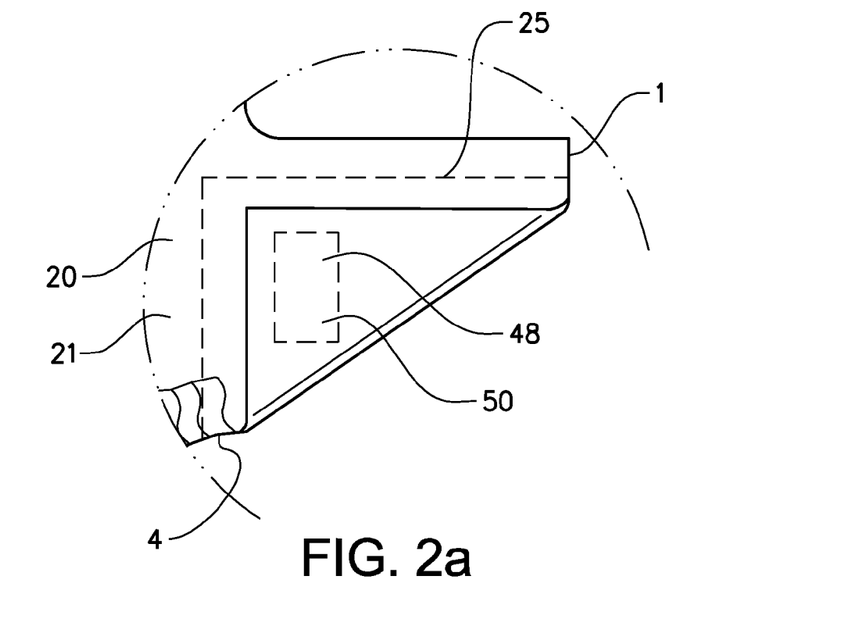
FIG. 2a shows an enlarged picture of how the corner circled in FIG. 1 has been folded in over the covering material in handling of the belt article.

FIG. 2a shows an enlarged picture of how the corner circled in FIG. 1 that is connected to the first transverse edge 4 and first longitudinal edge 1 of the belt article 10 has folded in over the first surface 21 of the covering layer 20. Since said corner comprises the area 25 having substantially reduced compatibility with the hook element 50, the corner does not in principle attach in its folded-in position. The corner probably recovers its unfolded configuration, therefore, or is at least easy to open manually and unfold. When front corners of previously known belt articles comprising fixing members provided with hook elements were folded in the manner described above, the hooks have powerfully attached to the loops densely present on the covering layer. It has become difficult thereby on the one hand to find the respective fixing member that has been concealed inside the respective folded corner and on the other hand to release the respective corner to be able to carry out application of the belt article to the user. It turned out that in most cases when a corner of a belt article 10 comprising fixing members 48, 49 folds in over the first surface 21 of the first covering layer 20, it is a relatively limited part of the respective corner that is folded. It is therefore sufficient to arrange relatively limited areas 25, 26 that have a substantially lower compatibility with the respective hook elements 50, 51 than adjacent parts of the first surface 21 of the first covering layer 20.

The areas 25, 26 have an extension in the article's longitudinal direction (X) substantially from the first transverse edge 4 to the opposing transverse edge 5 of 10-20%, preferably 15%, of the outstretched length of the belt article 10 in a longitudinal direction (X). In the transverse direction (Y) of the belt article, the first area 25 has an extension between the first longitudinal edge 1 and the longitudinal centre line 35 of the belt article 10 of 25-50%, preferably 37%, of the outstretched length of the first transverse edge 4 in a transverse direction (Y), and the second area 26 has an extension in the transverse direction (Y) of the article between the second longitudinal edge 2 and the centre line 35 of the article of 25-50%, preferably 37%, of the outstretched length of the first transverse edge 4 in the transverse direction (Y).

Outstretched length in the longitudinal direction (X) refers to the length that the belt article 10 has when the respective leg elastic 45 is stretched out from its substantially tension-free contracted state so that the first covering layer 20 has a smooth surface, i.e. the rippling that the covering layer 20 acquired when the respective leg elastic 45 was contracted has been eliminated. In the same way, outstretched length in a transverse direction (Y) refers to the length that the first transverse edge 4 of the belt article 10 has when the waist elastic 46 is stretched out from its substantially tension-free contracted state so that the first covering layer 20 has a smooth surface, i.e. the rippling that the covering layer 20 acquired when the respective waist elastic 46 was contracted has been eliminated.

According to an aspect of the invention, the relatively limited areas 25, 26 connected to the first and second fixing members 48, 49 entirely lack compatibility with the hook elements 50, 51, which means that the areas are entirely loop-free. The areas 25, 26 can consist in this case of thin plastic layers laminated onto the first surface 21 of the covering layer 20, for example. Alternatively, the covering layer 20 can be heat-treated, wherein all initially open surfaces within the areas 25, 26 for example by means of hot calendering. In other alternative belt articles 10 loop-free areas 25, 26 can have been created by sealing the areas that initially comprised loops with adhesive or the like.

Figure 2B:
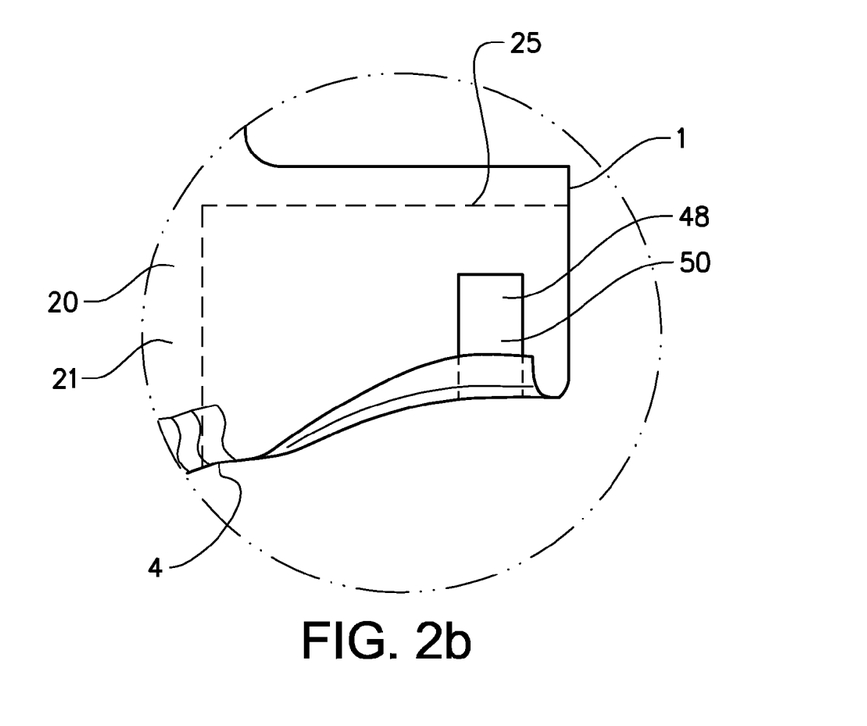
FIG. 2b shows an enlarged picture of how the corner circled in FIG. 1 has been folded in over the front fixing member.

FIG. 2b shows a commonly occurring situation when a small tab along the first transverse edge 4 of the belt article 10 has been accidentally folded in over the first hook element 50. Since said small tab mainly consists of the first liquid-permeable covering layer 20 and the second liquid-impermeable covering layer 30, the tab is extremely flexible, which is why it can be folded easily. Due to the fact that the folded tab has substantially lower compatibility with the hook element 50, the tab does not attach to the hooks of the hook element 50 in its folded configuration, wherein the entire surface of the fixing member is accessible for its purpose, i.e. to detachably attach the front end part 14 of the belt article 10 to the belt upon use.

Figure 3:
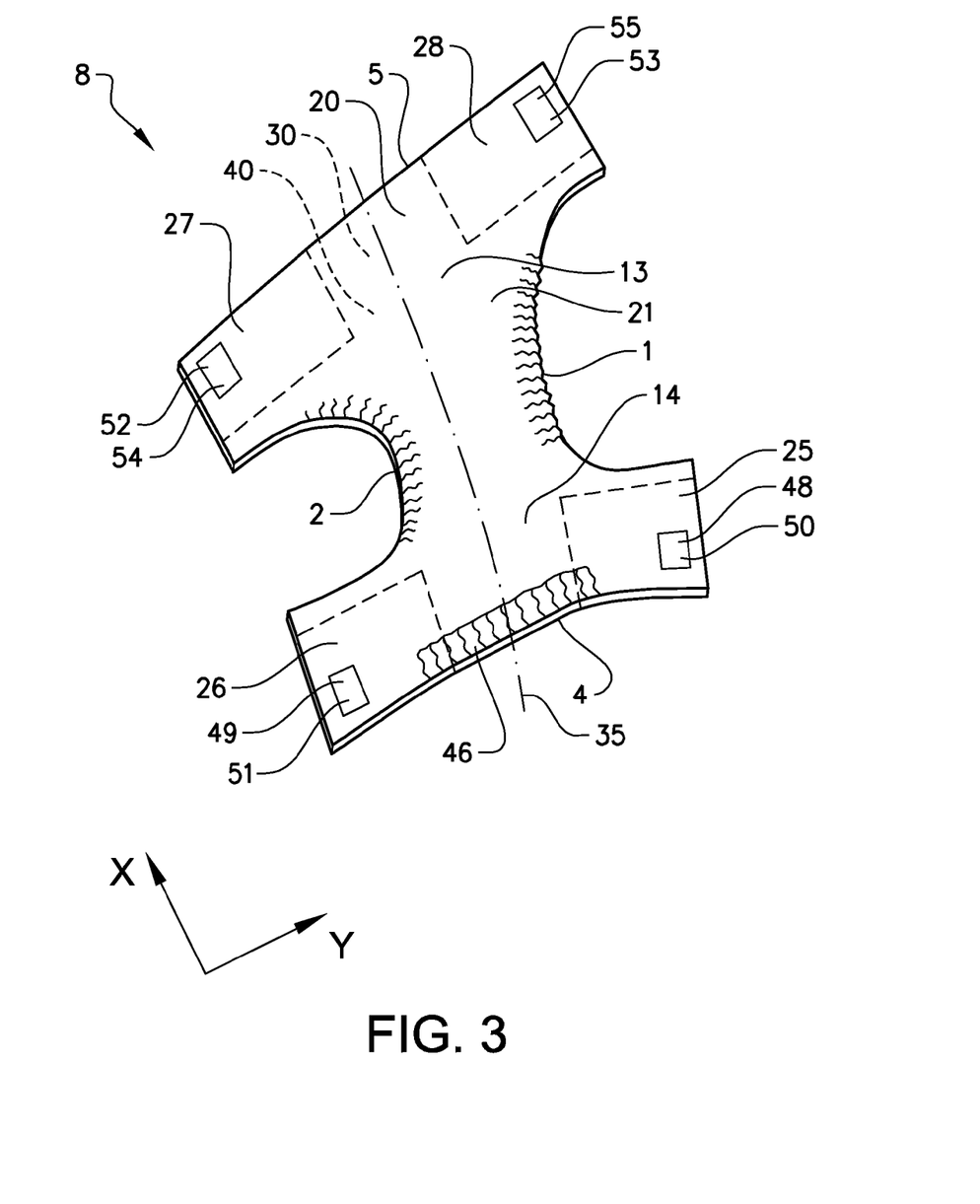
FIG. 3 shows an article intended to be fixed detachably to a separate belt arranged around a user's waist from the side that is intended to face towards the user when in use.

FIG. 3 shows another type of disposable article 8 in accordance with the invention, wherein the disposable article 8 is intended to be connected detachably to a separate belt that is applied around a user's waist. The disposable article 8 has a chassis comprising a first covering layer 20 constructed in the same way as the first covering layer 20 of the belt article 10.

The disposable article 8 can comprise a second covering layer 30 and an absorption body 40 in accordance with other aspects of the invention. The first covering layer 20, second covering layer 30 and the absorption body 40 are constructed and arranged here in the same way as they are constructed and arranged for the belt article 10 described above.

The disposable article 8 has an hourglass shape, but according to alternative aspects of the invention can have any shape, such as a rectangular shape, for example. The disposable article 8 has a front end part 14 comprising a first and a second fixing member 48, 49, wherein the fixing members have hook elements 50, 51. The fixing members 48, 49 are arranged connected to the two front corners of the covering layer 20. The front end part 14 also has a waist elastic 46 arranged in the transverse direction of the disposable article 8 alongside the first transverse edge 4. The covering layer 20 in the rear end part 13 of the disposable article 8 has a third and a fourth fixing member 52, 53 on the first surface 21. The fixing members 52, 53 have hook elements 54, 55. The fixing members 52, 53 are arranged against the second transverse edge 5, wherein the third fixing member 52 is arranged close to the second longitudinal edge 2 and the fourth fixing member 53 is arranged close to the first longitudinal edge 1, i.e. a fixing member 52, 53 in each rear corner of the disposable article 8. The disposable article 8 is substantially designed symmetrically and can therefore be turned with the rear end part 13 to the front on the user without any problem; the term back or front end part 13, 14 is intended more to distinguish the end parts in this description.

The disposable article 8 is distinguished primarily in that the first surface 21 of the first covering layer 20 comprises a first area 25 connected to the first fixing member 48, a second area 26 connected to the second fixing member 49, a third area 27 connected to a third fixing member 52 and a fourth area 28 connected to a fourth fixing member 53, wherein said areas 25, 26, 27, 28 have substantially lower compatibility with the respective hook elements 50, 51, 54, 55 than adjacent parts of the first surface 21 of the covering layer 20. The areas 25, 26, 27, 28 are all arranged to eliminate or at least reduce the tendency of the hook elements 50, 51, 54, 55 to attach against the first surface 21 of the first covering layer 20 when the corners of the disposable article 8 fold over said first surface 21 in the same way as described for the areas 25, 26 above.

Figure 4A:
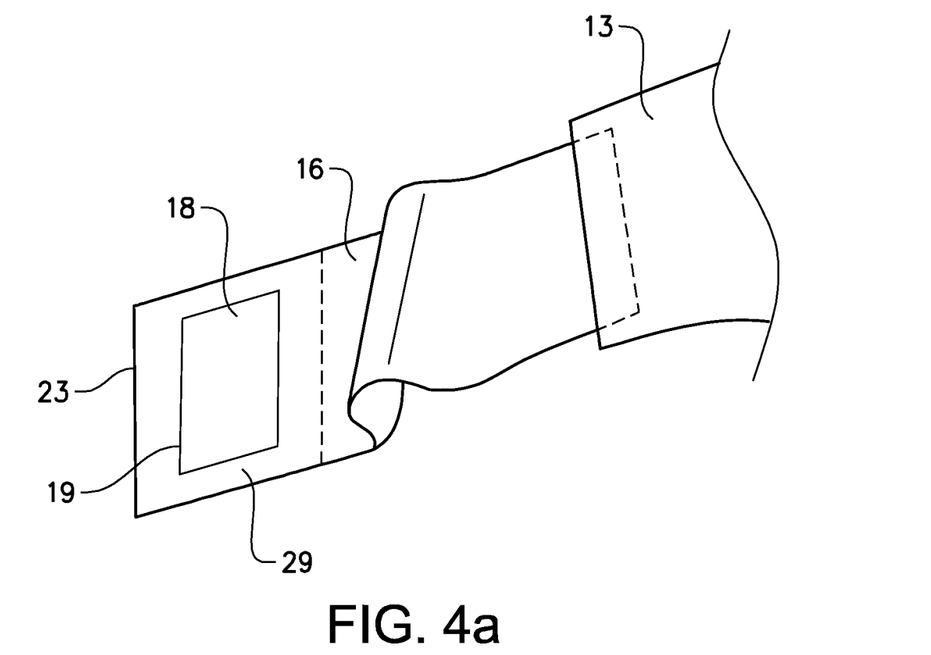
FIG. 4a shows an enlarged picture of the first belt half of the belt article in FIG. 1.

FIG. 4a shows an enlarged picture of the first belt half 16 of the belt article 10 in FIG. 1. The belt half 16 has a fixing member 18 comprising hooks. The fixing member 18 is intended to be connected detachably to the second belt half 17 when the belt 15 is applied around the waist of the user. The outer edge 19 of the fixing member 18 is arranged a small distance from the free end 23 of the belt half 16, but it also occurs that the outer edge 19 of the fixing member 18 coincides with the free end 23 of the belt half 16. It also occurs that the fixing member is as wide as the belt half 16 is wide.

Figure 4B:
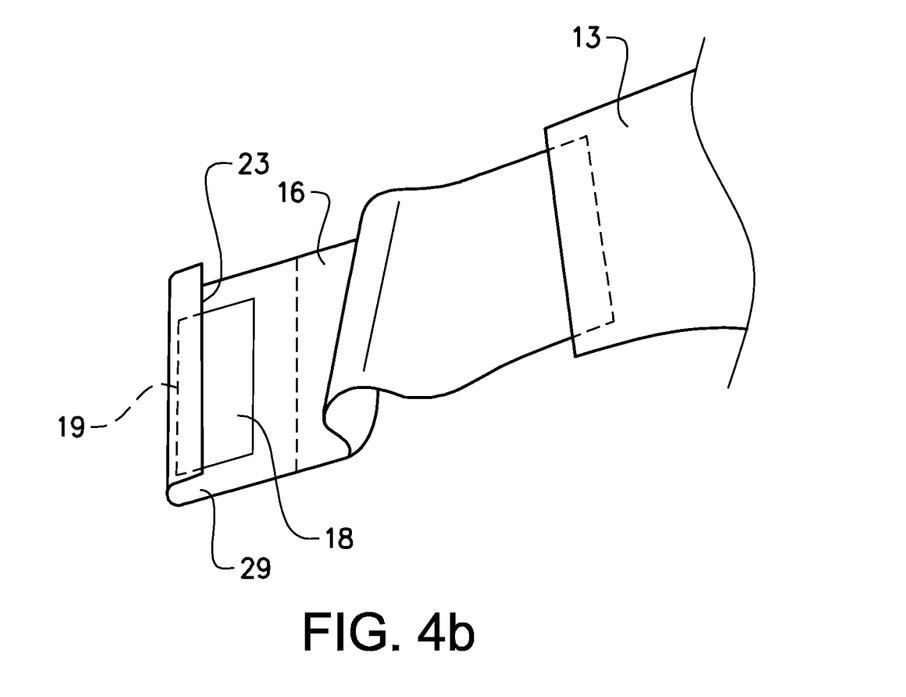
FIG. 4b shows an enlarged picture of the same belt half as in FIG. 4a when the outermost end of the belt half has been folded in over the fixing member on the belt.

FIG. 4b shows how the outermost part of the belt half 16, i.e. the part between the outer edge 19 of the fixing member 18 and the free end 23 of the belt half 16, accidentally folds over the fixing member 18 during handling. The outermost folded part can in this context easily attach on the hooks of the fixing member 18, but due to the fact that the part of the belt half 16 that surrounds the fixing member 18 comprises a loop-free area 29, the folded part is prevented from attaching on the hooks. Without said loop-free areas, it frequently happens that the folded part attaches on the hooks and is not noticed when the belt article 10 is to be applied to a user. The result is that only the part of the fixing member 18 that is not located under the folded part is used for its purpose, i.e. to fix the belt around the user's waist. The fixing of the belt diaper 10 on the user is impaired thereby, which in turn can mean that the belt article does not stay on the user after a while of use.

In cases where the outer edge 19 of the fixing member 18 coincides with the free end 23 of the belt half 16, it can happen that the entire outermost part of the belt including the fixing member 18 folds over the belt half 16, wherein it becomes hard to discover which of the two belt halves 16, 17 of the belt article 10 comprises the fixing member 18. It is also hard to release the folded part of the outermost part of the belt half 16 comprising the fixing member 18. In cases where the fixing member is as wide as the belt half 16 is wide, it is also hard to discover that a substantial part of the fixing member 18 has ended up under a part of the belt half that was accidentally folded over the fixing member. The invention also covers all conceivable combinations of the described aspects of the invention.

Furthermore, the invention is not limited to the aforesaid aspects, but is naturally applicable to other aspects within the scope of the following claims.

The invention claimed is:

1. A disposable article having a longitudinal direction, a longitudinal centre line and a transverse direction, wherein the article has a first longitudinal edge and a second longitudinal edge, a first transverse edge and a second transverse edge, wherein the article comprises a first covering layer comprising a first surface configured to face towards the user and a second surface configured to face away from the user in use, wherein at least a first fixing member and a second fixing member comprising hook elements are arranged on the first surface closer to the first transverse edge than to the second transverse edge, wherein the first fixing member is arranged closer to the first longitudinal edge than to the second longitudinal edge, and the second fixing member is arranged closer to the second longitudinal edge than to the first longitudinal edge, wherein parts of the first surface are mechanically compatible with the hook elements, wherein the article comprises a liquid-impermeable second covering layer arranged on the second surface of the first covering layer oriented away from the user, wherein an absorbent body is arranged between the first covering layer and the liquid-impermeable second covering layer and wherein the first covering layer is liquid-permeable, wherein the first surface of the first covering layer comprises first and second areas respectively connected to a corresponding one of the first and second fixing members, wherein each of said first and second areas has a lower mechanical compatibility with the respective hook elements of the corresponding one of the first and second fixing members than adjacent parts of the first surface of the covering layer.

2. The disposable article according to claim 1, wherein the areas having a lower mechanical compatibility with the respective hook elements have an extension in the longitudinal direction of the article from the first transverse edge to the opposing transverse edge of 10-20% of the outstretched length of the article, wherein the first area has an extension in the transverse direction of the article between the first longitudinal edge and the longitudinal centre line of the article of 25-50% of the outstretched length of the first transverse edge and wherein the second area has an extension in the transverse direction of the article between the second longitudinal edge and the centre line of the article of 25-50% of the outstretched length of the first transverse edge.

3. The disposable article according to claim 1, wherein the areas lack mechanical compatibility with the hook elements.

4. The disposable article according to claim 1, wherein the article is configured to be attached detachably to a separate belt arranged around a user's waist, wherein the article comprises a third and a fourth fixing member comprising hook elements arranged on the first surface closer to the second transverse edge than to the first transverse edge, wherein the third fixing member is arranged closer to the second longitudinal edge than to the first longitudinal edge and the fourth fixing member is arranged closer to the first longitudinal edge than to the second longitudinal edge, wherein the first surface of the first covering layer comprises a third area connected to the third fixing member and a fourth area connected to the fourth fixing member, wherein said areas have lower mechanical compatibility with the respective hook elements than adjacent parts of the first surface of the first covering layer.

5. The disposable article according to claim 4, wherein the third and fourth areas having lower mechanical compatibility with the respective hook elements have an extension in the longitudinal direction of the article from the second transverse edge to the opposing transverse edge of 10-20% of the outstretched length of the article, wherein the third area has an extension in the transverse direction of the article between the second longitudinal edge and the longitudinal centre line of the article of 25-50% of the outstretched length of the second transverse edge and wherein the fourth area has an extension in the transverse direction of the article between the first longitudinal edge and the centre line of the article of 25-50% of the outstretched length of the second transverse edge.

6. The disposable article according to claim 4, wherein the third and fourth areas lack mechanical compatibility with the hook elements.

7. The disposable article according to claim 4, wherein the third and fourth areas having lower mechanical compatibility with the respective hook elements have an extension in the longitudinal direction of the article from the second transverse edge to the opposing transverse edge of 15% of the outstretched length of the article, wherein the third area has an extension in the transverse direction of the article between the second longitudinal edge and the longitudinal centre line of the article of 37% of the outstretched length of the second transverse edge and wherein the fourth area has an extension in the transverse direction of the article between the first longitudinal edge and the centre line of the article of 37% of the outstretched length of the second transverse edge.

8. The disposable article according to claim 1, wherein the article comprises a belt arranged connected to the article's second transverse edge, wherein the belt is configured to be fastened around the user's waist upon use, wherein the hook elements are configured upon use to be connected detachably to the surface of the belt oriented away from the user.

9. The disposable article according to claim 1, wherein the first covering layer consists of a nonwoven material comprising heat-treatable synthetic fibres having loops on the first surface, wherein the loops in the respective area having lower mechanical compatibility with the respective hook elements have been reduced by heat treatment.

10. The disposable article according to claim 1, wherein the first covering layer consists of a nonwoven material having loops on the first surface, wherein the loops in the respective area having lower mechanical compatibility with the respective hook elements have been eliminated by laminating a cover layer free of loops on the first surface in the respective area.

11. The disposable article according to claim 10, wherein the cover layers consist of a spunbond nonwoven.

12. The disposable article according to claim 10, wherein the cover layers consist of a plastic film.

* * * * *